(12) United States Patent
Van Venrooij et al.

(10) Patent No.: US 7,212,867 B2
(45) Date of Patent: May 1, 2007

(54) DIRECTIONAL BRAIN STIMULATION AND RECORDING LEADS

(75) Inventors: Paul Van Venrooij, Hoensbroek (NL);
Frans H. Gielen, Eckelrade (NL);
Keith R. Mullett, Valkenburg (NL);
Victor Duysens, Grevenbicht (NL);
Dan Gruia, Friesoythe (NL)

(73) Assignee: Medtronic, Inc., Minneapolis, MN (US)

( * ) Notice: Subject to any disclaimer, the term of this patent is extended or adjusted under 35 U.S.C. 154(b) by 30 days.

(21) Appl. No.: 10/008,773

(22) Filed: Dec. 5, 2001

(65) Prior Publication Data

US 2002/0183817 A1 Dec. 5, 2002

Related U.S. Application Data

(60) Provisional application No. 60/254,281, filed on Dec. 7, 2000.

(51) Int. Cl.
*A61N 1/05* (2006.01)

(52) U.S. Cl. ..................................................... 607/116

(58) Field of Classification Search ................. 607/373, 607/377, 378, 544, 545, 115, 116, 117, 118, 607/122; 600/115–118, 373, 377, 378, 544, 600/545
See application file for complete search history.

(56) References Cited

U.S. PATENT DOCUMENTS

| 452,220 | A | 5/1891 | Gunning |
| 3,474,791 | A | 10/1969 | Bentov |
| 3,485,247 | A | 12/1969 | Ackerman |

(Continued)

FOREIGN PATENT DOCUMENTS

| EP | 0234457 | 5/1993 |
| EP | 0580928 | 2/1994 |
| EP | 0832667 A2 | 4/1998 |
| EP | 0 998 958 B1 | 5/2000 |
| EP | 1048317 A2 | 11/2000 |
| EP | 1048317 | 11/2000 |
| EP | 1201198 | 5/2002 |
| FR | 2537874 | 10/1983 |
| GB | 1147532 | 4/1969 |
| GB | 1453424 | 10/1976 |
| WO | WO 87/01947 | 4/1987 |
| WO | WO 99/36122 | 7/1999 |
| WO | WO 99/43031 | 8/1999 |
| WO | WO 99/49934 | 10/1999 |
| WO | WO 99/62591 | 12/1999 |
| WO | WO 01/08744 | 2/2001 |
| WO | WO 01/58519 | 8/2001 |
| WO | WO 2002/068042 | 9/2002 |

OTHER PUBLICATIONS

Xu, Shi–Ang; Xu, Jin : McAnally, Ken I.; and Clark, Graeme M., *Comparison of Half–Band And Full–Band Electrodes For Intracochlear Electrical Stimulation*, Ann. Otol. Rhinol. Laryngol., 102: 363–367 (1993).
PCT International Search Report, PCT/US/02/09895 (Nov. 25, 2002).

*Primary Examiner*—George Manuel
(74) *Attorney, Agent, or Firm*—Michael J. Jaro; Thomas F. Woods; Stephen W. Bauer

(57) ABSTRACT

A directional brain stimulation lead assembly provides a lead body and an insulating member defining one or more windows that selectively expose portions of electrodes carried by the lead body to produce a directional stimulation current field. The lead assembly can achieve more effective localization of electrical stimulation to very small brain targets, and thereby reduce the incidence of material side effects caused by collateral stimulation of brain tissue adjoining a desired brain target. In addition, the directional lead can sense brain activity on a more localized basis.

14 Claims, 16 Drawing Sheets

U.S. PATENT DOCUMENTS

| | | | |
|---|---|---|---|
| 3,646,940 A | 3/1972 | Timm et al. | |
| 3,911,928 A | 10/1975 | Lagergren | |
| 3,949,757 A | 4/1976 | Sabel | |
| 3,974,834 A | 8/1976 | Kane | |
| 4,735,205 A | 4/1988 | Chachques et al. | |
| 4,744,370 A | 5/1988 | Harris | |
| 4,903,702 A | 2/1990 | Putz | 600/377 |
| 4,961,434 A | 10/1990 | Stypulkowski | |
| 5,000,194 A | 3/1991 | van den Honert et al. | |
| 5,029,585 A | 7/1991 | Lieber et al. | |
| 5,114,744 A | 5/1992 | Cloutier et al. | |
| 5,127,403 A | 7/1992 | Brownlee | |
| 5,265,608 A | 11/1993 | Lee et al. | 600/377 |
| 5,374,285 A | 12/1994 | Vaiani et al. | |
| 5,405,373 A | 4/1995 | Petersson et al. | |
| 5,423,877 A | 6/1995 | Mackey | |
| 5,455,998 A | 10/1995 | Miyazono et al. | |
| 5,456,254 A | 10/1995 | Pietroski et al. | |
| 5,489,275 A | 2/1996 | Thompson et al. | |
| 5,501,703 A | 3/1996 | Holsheimer et al. | |
| 5,562,722 A | 10/1996 | Racz et al. | |
| 5,578,067 A | 11/1996 | Ekwall et al. | |
| 5,643,339 A | 7/1997 | Kavteladze et al. | |
| 5,649,970 A | 7/1997 | Loeb et al. | |
| 5,713,944 A | 2/1998 | Kroll | |
| 5,755,761 A * | 5/1998 | Obino | 607/122 |
| 5,800,465 A | 9/1998 | Thompson et al. | |
| 5,824,030 A | 10/1998 | Yang et al. | |
| 5,843,148 A | 12/1998 | Gijsbers et al. | |
| 5,895,416 A | 4/1999 | Barreras, Sr. et al. | |
| 5,913,882 A | 6/1999 | King | |
| 5,919,222 A | 7/1999 | Hjelle et al. | |
| 5,927,277 A | 7/1999 | Baudino et al. | |
| 6,011,996 A | 1/2000 | Gielen et al. | |
| 6,038,480 A | 3/2000 | Hrdlicka et al. | |
| 6,052,608 A | 4/2000 | Young et al. | |
| 6,052,624 A | 4/2000 | Mann | |
| 6,134,478 A | 10/2000 | Spehr | |
| 6,178,354 B1 | 1/2001 | Gibson | |
| 6,212,434 B1 | 4/2001 | Scheiner et al. | |
| 6,240,320 B1 | 5/2001 | Spehr et al. | |
| 6,253,109 B1 | 6/2001 | Gielen | |
| H1905 H | 10/2001 | Hill | |
| 6,319,241 B1 | 11/2001 | King et al. | |
| 6,466,811 B1 | 10/2002 | Hassett | |
| 6,473,653 B1 | 10/2002 | Schallhorn et al. | |
| 6,493,590 B1 | 12/2002 | Wessman et al. | |
| 6,510,347 B2 | 1/2003 | Borkan | |
| 6,526,321 B1 | 2/2003 | Spehr | |
| 6,587,733 B1 | 7/2003 | Cross, Jr. et al. | |
| 6,666,864 B2 | 12/2003 | Bencini et al. | |
| 6,721,604 B1 | 4/2004 | Robinson et al. | |
| 2001/0053885 A1 | 12/2001 | Gielen et al. | |
| 2002/0022872 A1 | 2/2002 | Gielen et al. | |
| 2002/0027336 A1 | 3/2002 | Ross et al. | |
| 2003/0083724 A1 | 5/2003 | Jog et al. | |

\* cited by examiner

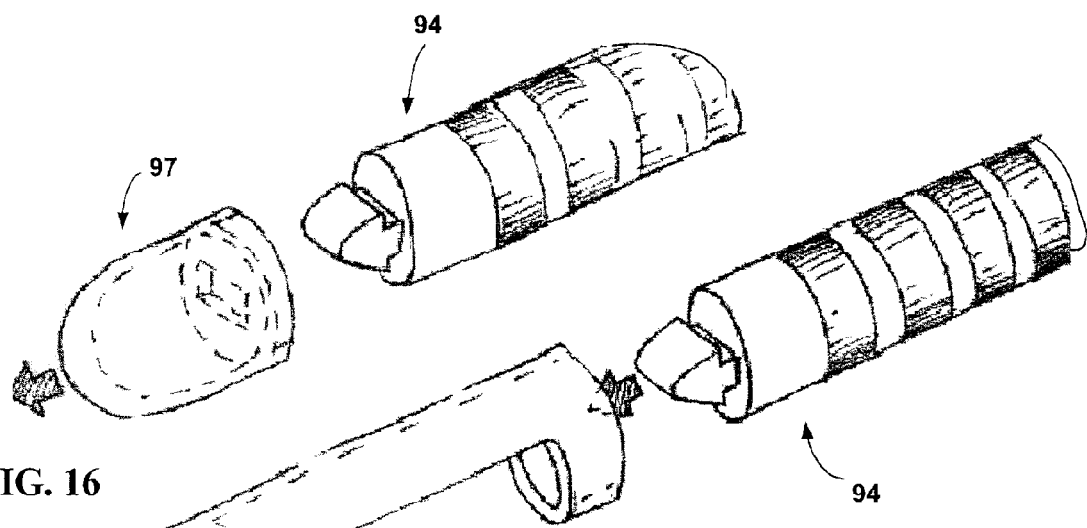
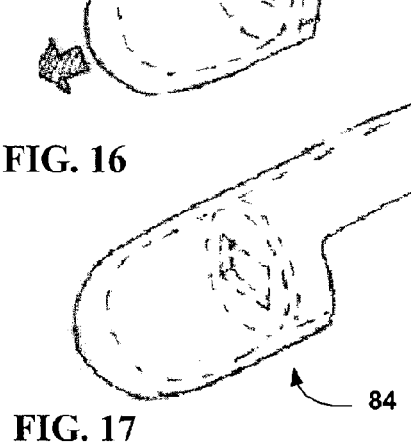
FIG. 16
FIG. 17

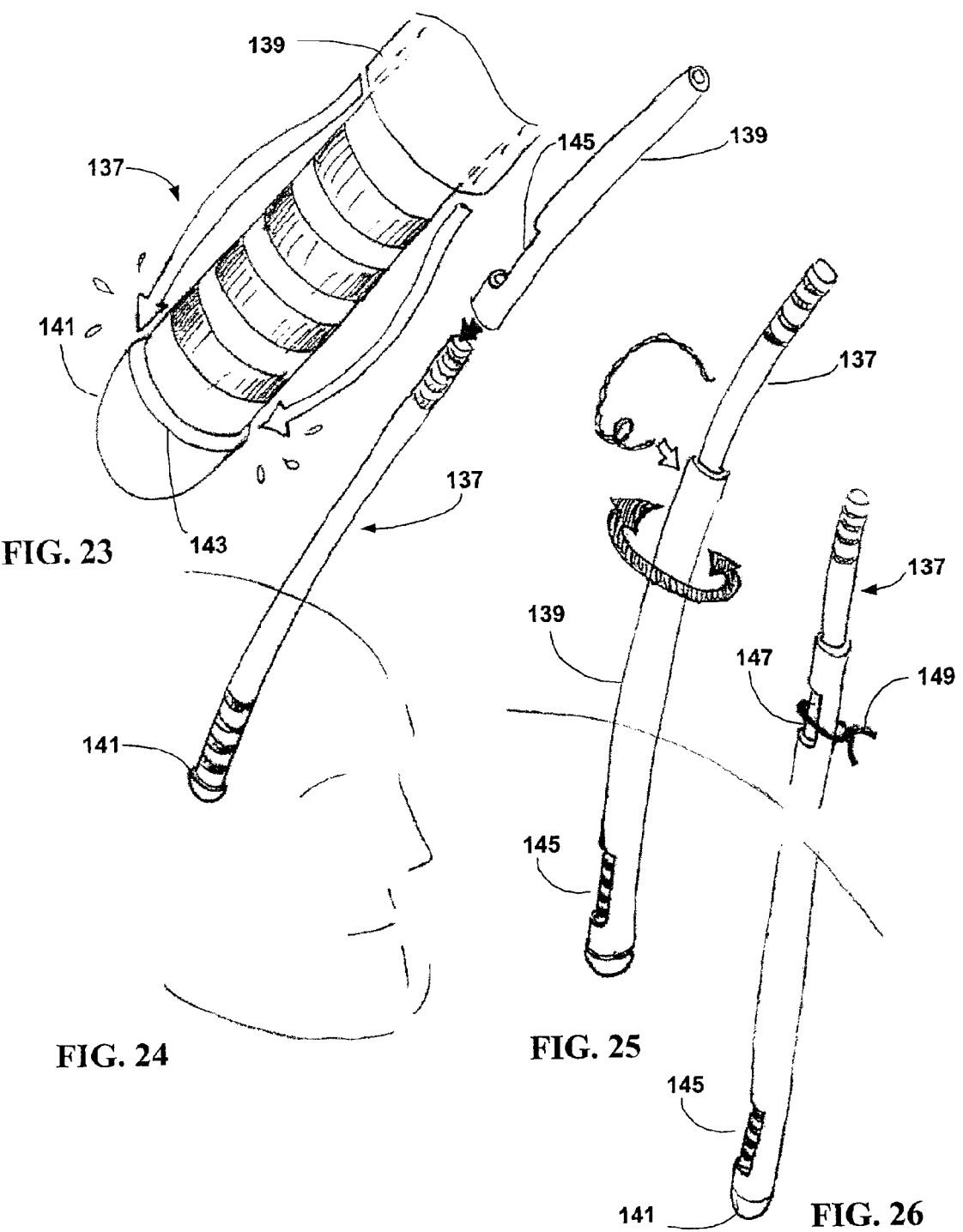

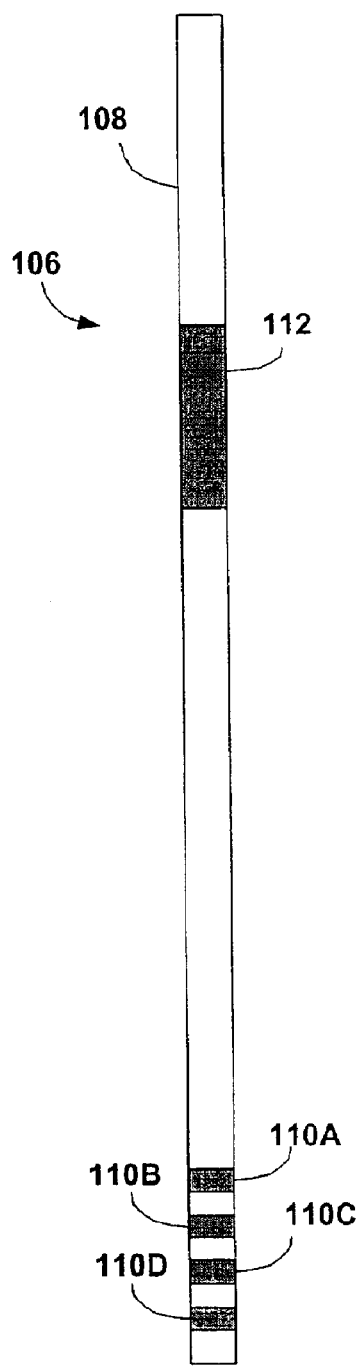
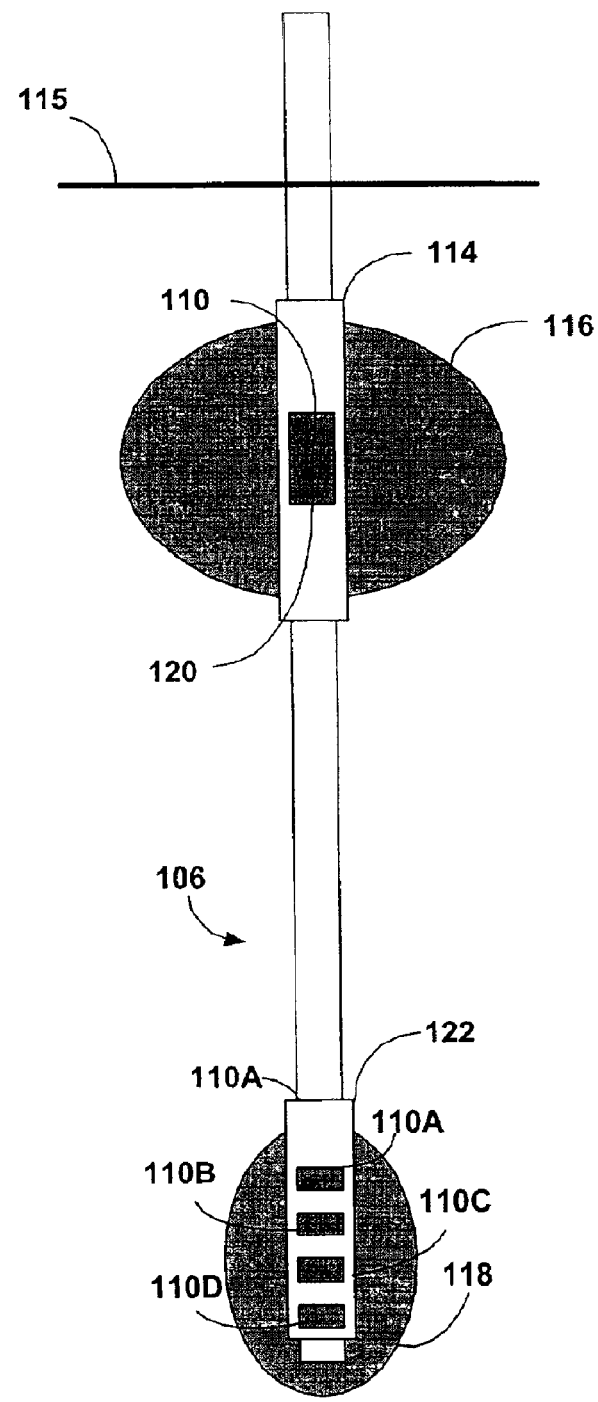
FIG. 29　　　　　FIG. 30

DIRECTIONAL BRAIN STIMULATION AND RECORDING LEADS

This application claims priority from U.S. provisional application Ser. No. 60/254,281, filed Dec. 7, 2000, the entire content of which is incorporated herein by reference.

FIELD OF THE INVENTION

This invention relates to brain stimulation and recording and, more particularly, electrical leads useful in brain stimulation and recording.

BACKGROUND OF THE INVENTION

Deep brain stimulation (DBS) leads are used to stimulate nerve structures in specific areas of the brain to either excite or inhibit cell activity. A stimulation lead is implanted at a precise location within the brain using CT or MRI imaging techniques and stereotactic guidance. Once implanted, the stimulation lead delivers electrical stimulation to produce nerve impulses that inhibit symptoms of a brain disorder. For example, deep brain stimulation can be effective in the management of chronic pain of neuropathic and or nociceptive origin. In addition, deep brain stimulation can be used to treat movement disorders, such as Parkinsons Disease, as well as epilepsy and psychiatric disorders.

Precise placement of the stimulation lead within the brain is extremely important. In some applications, the stimulation lead must be positioned to deliver stimulation exclusively to a very small brain target without stimulating adjacent brain tissue. Precision is extremely important, for example, in SubThalamic Nucleus (STN) stimulation and Globus Pallidus internal (Gpi) stimulation. If stimulation is not delivered with precision to a desired brain target, adjoining areas may likewise be stimulated, leading to side effects that are not well tolerated by the patient.

Also, existing deep brain stimulation leads are typically equipped with cylindrical electrode rings. Stimulation current spreads approximately spherically around the cylindrical electrodes in a homogeneous and isotropic medium. In this situation, the electrode contact is the center of the sphere. However, the three-dimensional, functional structures of the brain may not coincide with the approximately spherical configuration of the stimulation current. As a result, the shape of the stimulation current can make localized stimulation of a desired target difficult.

Existing stimulation leads and positioning techniques can be limited in their ability to effect precise localized stimulation of very small brain targets. Accordingly, there is a need for deep brain stimulation leads that are better suited to stimulate selected small brain targets on a exclusive basis. More generally, there is a need for deep brain stimulation leads capable of delivering appropriate stimulation to very small brain targets without causing intolerable side effects.

Others have developed electrical leads for delivery of stimulation to localized regions in the human body. Unfortunately, the effectiveness of such leads has been challenged by applications involving extremely small targets within the human brain. Table 1 lists a number of documents that disclose electrical leads designed to achieve electrical stimulation in small, localized regions.

TABLE 1

| Patent Number | Inventors | Title |
| --- | --- | --- |
| U.S. Pat. No. 5,843,148 | Gijsbers et al. | High Resolution Brain Stimulation Lead and Method of Use |
| U.S. Pat. No. 5,643,339 | Holsheimer | Multichannel Apparatus for Epidural Spinal Cord Stimulation |
| U.S. Pat. No. 5,501,703 | Holsheimer | Multichannel Apparatus for Epidural Spinal Cord Stimulation |
| US/01/27336 | Gielen et al. | Combined Micro-macro Brain Stimulation Lead and Method of Using Same |
| U.S. Pat. No. 4,961,434 | Stypulkowski | Array of Recessed Radially Oriented Bipolar Electrodes |
| U.S. Pat. No. 5,000,194 | van den Honert | Array of Bipolar Electrodes |
| U.S. Pat. No. 5,927,277 | Baudino et al. | Method and Apparatus for Securing Probes Within a Burr Hole |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY OF THE INVENTION

The present invention has certain objects. That is, various embodiments of the present invention may provide solutions to one or more problems existing in the prior art with respect to the treatment of neurological disorders, and with respect to the delivery of electrical stimulation to the brain generally using implantable stimulation leads, including deep brain stimulation leads. Such problems may include, for example, delivery of electrical stimulation to desired targets within the brain with precision using deep brain stimulation leads, delivery of electrical stimulation to desired targets on a highly localized basis to the general exclusion of adjoining brain tissue, delivery of electrical stimulation to desired targets to thereby achieve a desired therapeutic response without causing undesirable side effects, and delivery of electrical stimulation to desired targets without the need for extensive repositioning of a deep brain stimulation lead. Various embodiments of the present invention may have the object of solving at least one of the foregoing problems.

In addition, various embodiments of the present invention may have the object of improving the ability to sense and record electrical activity in localized regions of the b rain. For example, the present invention may address problems involving the recording of brain activity from small functional brain targets on a highly localized basis with less interference caused by activity in adjoining tissue within the brain. Accordingly, the present invention also may address problems involving the accuracy of recording signals from small functional brain targets.

The present invention has certain advantages. That is, in comparison to known implementations for delivering electrical stimulation to the brain, various embodiments of the present invention may provide one or more advantages. Such advantages may include, for example, more effective localization of electrical stimulation to very small brain targets, reduction of electrical stimulation of brain tissue adjoining a desired brain target, reduction in material side effects as a result of collateral stimulation of brain tissues adjoining a desired brain target, reduction in the need for lead tip repositioning relative to a desired brain target, flexibility in shaping and steering of electrical stimulation current emitted by a stimulation lead, flexible configuration and deployment of a stimulation lead as a function of the specific target characteristics identified by a surgeon, and ease of manufacture and cost effectiveness of stimulation leads providing any of the foregoing advantages.

As added advantages, various embodiments of the present invention may improve the ability to sense and record electrical activity in localized regions of the brain. For example, the present invention may be used to record brain activity from small functional brain targets on a highly localized basis with less interference caused by activity in adjoining tissue within the brain, contributing to increased accuracy in the recorded signals.

he present invention has certain features. In particular, various embodiments of the present invention may have one or more of the following features: an electrical lead assembly having a lead body with an electrode, and an electrically insulating member that extends over the lead body and defines a window that exposes a portion of the electrode; an electrical lead assembly having a lead body with a plurality of stimulation electrodes, and an electrically insulating member that extends over the lead body and defines a plurality of windows that expose portions of the electrodes; an electrical lead assembly having a lead body with a plurality of stimulation and recording electrodes, and an electrically insulating member that extends over the lead body and defines a plurality of windows that expose portions of the electrodes; and a method for producing directional output from an electrical stimulation lead that involves forming an insulating member over a lead body, and positioning the insulating member relative to the lead body so that a window formed in the insulating member exposes a selected portion of the electrode.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 16 is a perspective view of another stimulation lead.

FIG. 17 is another perspective view of the lead assembly of FIG. 15.

FIG. 23 is a perspective view of a lead assembly with a shouldered tip.

FIG. 24 is a perspective view of the lead assembly of FIG. 23 in combination with an insulating member.

FIGS. 25 and 26 illustrate the lead assembly of FIG. 23 in operation.

FIG. 29 is a side view of an electrical stimulation lead with distal and intermediate electrodes in accordance with another embodiment.

FIG. 30 is a side view of the lead of FIG. 29 incorporating a windowed insulating member that is slidable to expose a portion of an intermediate electrode.

DETAILED DESCRIPTION OF THE PREFERRED EMBODIMENTS

Figure 1:
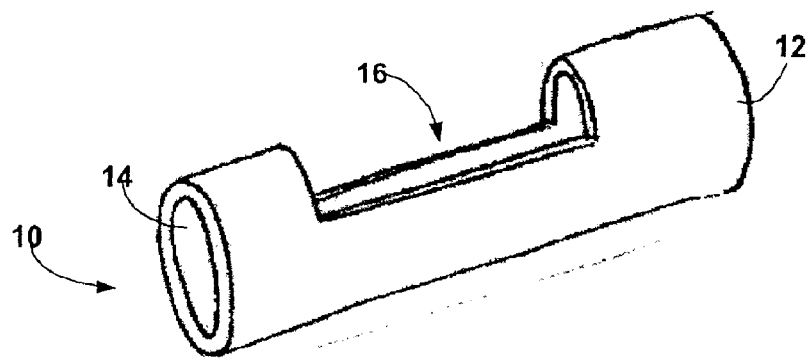
FIG. 1 is a perspective view of a windowed insulating member for use with a brain stimulation lead in accordance with a first embodiment.

In the following detailed description of the preferred embodiments, reference is made to the accompanying drawings that form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims. FIG. 1 is a perspective view of a windowed insulating member 10 for use with a deep brain stimulation lead in accordance with a first embodiment. As shown in FIG. 1, insulating member 10 has a substantially tubular body 12 defining an inner lumen 14 that extends axially along the length of the tubular body. Tubular body 12 also defines a window 16, i.e., an aperture, that permits access to inner lumen 14 from outside of the tubular body. As will be described, window 16 is sized and positioned to expose a portion of one or more electrodes carried by a brain stimulation lead, such as a deep brain stimulation lead, facilitating directional application of electrical stimulation to a desired target within the brain. Insulating member 10 is formed from an electrically insulative material. In general, portions of an electrode covered by insulating member 10 will be electrically insulated, whereas portions of an electrode exposed by window 16 will be capable of making contact with tissue and conducting stimulation current.

Tubular body 12 may be formed from a variety of materials including various biocompatible plastics and other insulative materials. For example, tubular body 12 may be formed from polyurethane, pellethane, or the like. Window 16 may be cut from or machined within a length of tubing to form insulating member 10. Alternatively, insulating member 10 can be formed by injection molding, vulcanization molding, or the like. In each case, the resulting insulating member 10 is structured and sized for attachment to deep brain stimulation lead, e.g., at the distal tip. In addition, insulating member 10 has a wall thickness sufficiently small to permit clearance for implantation in the brain, but sufficiently large to retain electrically insulative properties and avoid electrical breakdown when in contact with a stimulation electrode.

Figure 2:
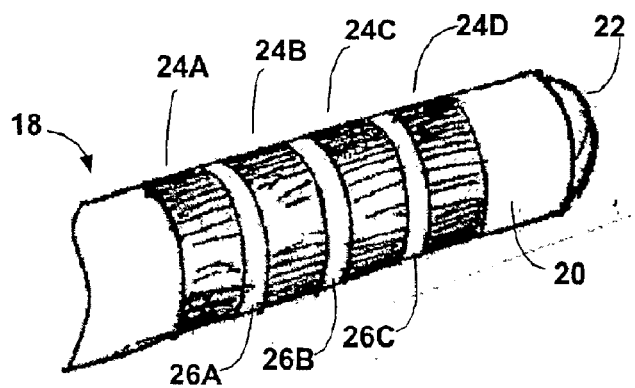
FIG. 2 is a perspective view of a brain stimulation lead.

FIG. 2 is a perspective view of a deep brain stimulation lead 18. As shown in FIG. 2, lead 18 has an elongated lead body 20 and a distal tip 22. Lead body 20 is tubular in form and may have a substantially circular cross-section. Lead 18 has a proximal end (not shown) with connectors for connecting to a stimulation current generator. Lead body 20 may be formed from a biocompatible material such as polyurethane. One or more stimulation electrodes 24A, 24B, 24C, 24D (hereinafter 24) may be distributed along the length of lead body 20 adjacent distal tip 22. Electrodes 24 may be separated by gaps 30 26A, 26B, 26C. Each electrode 24 can be made from an electrically conductive, biocompatible material such as platinum iridium and embedded into lead body 20. In addition, one or more of electrodes 24 may function as recording electrodes to monitor internal brain signals. Although lead body 20 in FIG. 2 represents a quadri-polar lead configuration, uni-, bi-, tri- and multi-polar lead configurations are envisioned for application of the present invention. Moreover, for some therapies, lead body 20 may be equipped with even larger numbers of leads, particularly when the lead is used for both stimulation and recording. For example, in some embodiments, lead body 20 may carry one, two, four, six, eight, ten, twelve, fourteen, or even sixteen electrodes. In addition, lead body 20 may carry odd numbers of electrodes, especially when recording is involved. In some embodiments, a reference potential may be provided not by the electrodes carried on lead body 20, but by an external reference electrode or a contact surface on an implanted pulse generator or the like.

Each electrode 24 may form a substantially cylindrical ring of conductive material that extends about an exterior wall of lead body 20. For example, an electrode 24 may extend the entire 360 degrees about lead body 20 or some lesser extent. In some embodiments, lead body 20 may be tubular but not necessarily cylindrical. For example, its electrodes 24, insulating member 10, and lead body 20 may have alternative cross sections, e.g., square, rectangular, oval or the like. In general, the structure and arrangement of lead 18 and electrodes 24 may be substantially similar to that of the Model 3387 or Model 3389 DBS leads commercially available from Medtronic, Inc. of Minneapolis, Minn. The Model 3387 and 3389 DBS leads are described in detail in the Lead Kit for Deep Brain Stimulation (3387/89 Lead Kit) Implant Guide, available from Medtronic, Inc., the entire content of which is incorporated herein by reference. In some cases, insulating member 10 may increase the overall diameter of lead 18 enough to require a larger introducer size. In that case, a larger insertion needle may be selected, along with a larger support on the stereotactic frame used for lead placement.

In some embodiments, insulating member 10 may form part of an electrical lead kit in combination with lead body 20 and material for adhering the insulating member to the lead body. For example, an electrical lead kit may include lead body 20 and a variety of different insulating members 10 with different window configurations or patterns designed to be selected by a surgeon to achieve a desired directional effect. In this case, the surgeon or a technician would prepare lead 18 by placing insulating member 10 in a desired position relative to the electrodes 24 carried by lead body 20, and then bond the insulating member with the lead body, e.g., using an adhesive.

Figure 3:
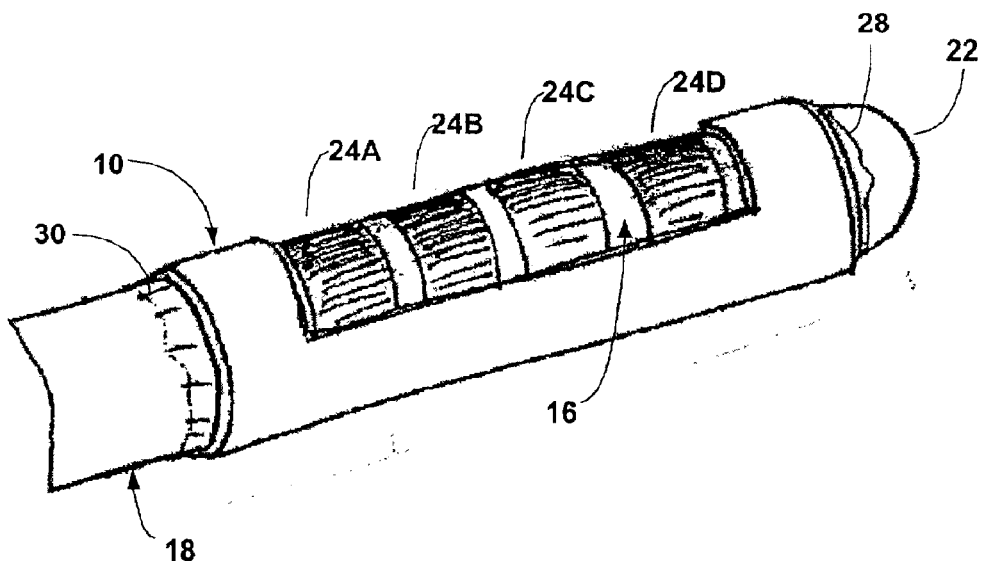
FIG. 3 is perspective view illustrating a lead assembly incorporating the windowed insulating member of FIG. 1 and the brain stimulation lead of FIG. 2.

FIG. 3 is perspective view illustrating a lead assembly incorporating the windowed insulating member 10 of FIG. 1 and lead 18 of FIG. 2. In the example of FIG. 3, insulating member 10 is placed over distal tip 22 of lead body 20 and fixed in place relative to electrodes 24. In particular, insulating member 10 is positioned so that window 16 exposes portions of a desired number of electrodes 24. Insulating member 10 may be fixed in place on lead 18 by adhesive bonding or ultrasonic welding. In the example of FIG. 3, if insulating member 10 and lead 18 are formed from polyurethane, a polyurethane solution may be used to dissolve adjacent bonding surfaces and create a bond. Bonding surfaces 28, 30 may be provided at opposite ends of insulating member 10.

The exposed portions of electrodes 24 are capable of delivering electrical stimulation current through window 16 to adjacent brain tissues when lead 18 is positioned relative to a desired target within the brain. The stimulation current may be applied to excite or inhibit cell activity within the brain and thereby alleviate symptoms of a brain disorder. Window 16 permits contact between limited portions of electrodes 24 and brain tissue. Insulating member 10 acts as an insulative cover for other portions of electrodes 24, however, limiting the tissue to which the electrical stimulation current is delivered. In this manner, window 16 of insulating member 10 helps to define a more localized area for delivery of electrical stimulation current, making lead 18 more directional.

Due to the wall thickness of insulating member 10, when formed as a separated sleeve-like member, window 16 may create a recessed electrode surface. The shape of window 16 may vary. For example, window 16 may be substantially rectangular, square, circular, or oval-shaped, depending upon the desired effect of window 16 in shaping the stimulation current field. Thus, the shape and size of window 16 may vary to achieve targeted electrode surface areas and shapes, as well as electrode spacing and electrode orientation. Other techniques for applying insulating member 10 to lead body 20 may be used. In some embodiments, insulating member 10 may be applied directly to lead body 20. For example, insulating member 10 could be applied to lead body 20 by insert-molding, dip coating following by etching, scribing, or cutting to define window 16, or selective vapor deposition of materials such as parylene to form a patterned coating that defines one or more windows.

The use of insulating member 10 can improve the efficacy of deep brain stimulation treatment. When the approximately spherical stimulation current field of a cylindrical electrode does not coincide with the desired functional brain target, a surgeon ordinarily needs to reposition the lead to avoid sub-optimal lead placement and resultant problems in achieving precise, localized treatment. A mismatch between the current field and brain structure may result from positioning inaccuracies in the surgical procedure or from the particular pathological three-dimensional brain structure of interest. Infarcted or damaged tissue, as well as tumors or bleeding tissues, may complicate positioning and conformance of the electrical stimulation current field to the desired target.

Insulating member 10 transforms lead 18 into a directional deep brain stimulation lead, however, and thereby allows selective orientation of the stimulation current. In some instances, the surgeon may be able to achieve successful stimulation without repositioning lead 18 with the patient's brain. Repositioning is generally undesirable due to the risks involved in repeated brain penetrations. In addition, insulating member 10 can be selected and applied to produce stimulation current fields that better conform to the desired brain target. Also, it is possible that effective stimulation can be delivered with reduced stimulation currents. In other words, it may not be necessary to apply the increased stimulation currents that are sometimes necessary due to inaccurate positioning of the lead relative to the target.

Directional application of electrical stimulation current can be highly desirable for a number of reasons. For example, more effective localization of electrical stimulation reduces electrical stimulation of brain tissue adjoining a desired brain target, and can significantly reduce the incidence of undesirable side effects caused by electrical stimulation. In addition, the directional capabilities of lead 18 in combination with insulating member 10 can be effective in reducing the need for lead tip repositioning by a surgeon relative to a desired brain target in order to achieve desired effects or eliminate undesired effects. Also, insulating member 10 provides the surgeon with flexibility in shaping the electrical stimulation energy emitted by lead 18. In some embodiments, the surgeon may be able to select one of several configurations and positions for insulating member 10 as a function of the specific target characteristics at hand. Moreover, insulating member 10 provides ease of manufacture, enabling directionality to be achieved by, in effect, retrofitting existing lead structures with cylindrical electrodes.

Figure 4:
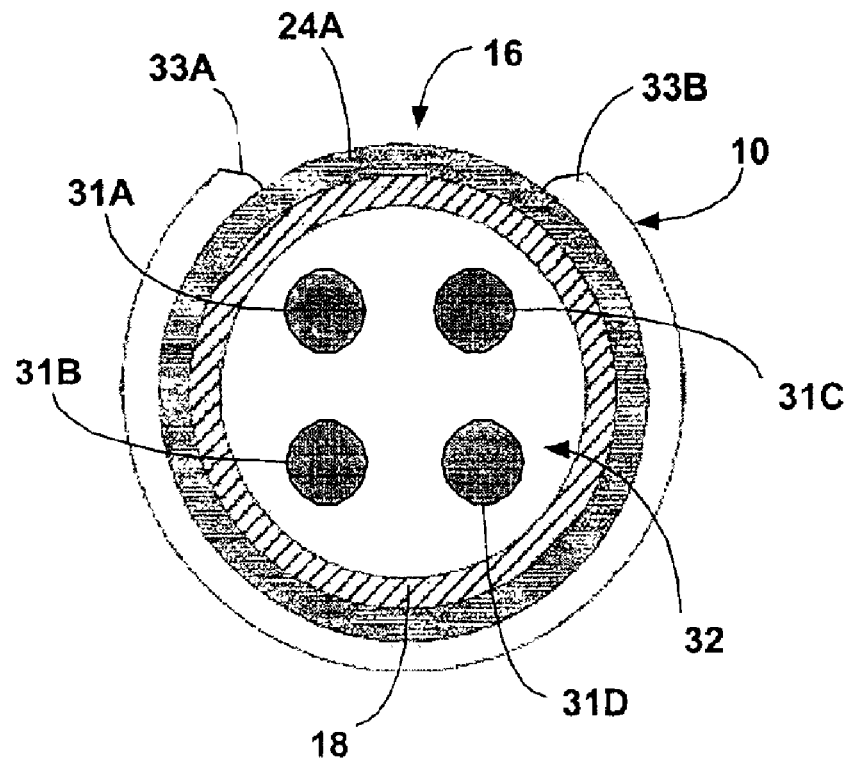
FIG. 4 is a cross-sectional view of the lead assembly of FIG. 3.

FIG. 4 is a cross-sectional view of the lead assembly of FIG. 3. As shown in FIG. 4, lead body 18 defines an inner lumen that carries one or more electrical conductors 31A, 31B, 31C, 31D (hereinafter 31). Electrical conductors 31 carry electrical stimulation current from a stimulation current generator (not shown) to electrodes 24. Each electrode 31 may form part of a multi-conductor coil, with each conductor being individually insulated. Electrodes 31 may be coupled to respective electrodes 24 by welded connections. In general, there may be one conductor 31 for each electrode 24. In some embodiments, however, two or more redundant conductors 31 may be provided for each electrode 24 to promote reliability.

As further shown in FIG. 4, window 16 exposes only a portion of the cylindrical ring electrode 24A. Window 16 defines edges 33A, 33B at opposite sides of the window. Notably, as shown in FIG. 4, edges 33A, 33B preferably are formed with a generally smooth, or "rounded," profile. In this way, as lead 18 is rotated following implantation, the rounded profiles of edges 33A, 33B are less likely to cause trauma to surrounding tissue. Similarly, it may be generally desirable that edges at the proximal and distal ends of insulating member 10 be formed with smooth profiles to avoid trauma during axial movement of lead 18.

To promote directionality, window 16 may be sized to expose less than or equal to approximately 180 degrees of the extent of electrode 24A. For enhanced directionality, window 16 may be sized to expose between approximately 110 and 130 degrees of the extent of electrode 24A, and preferably approximately 120 degrees. In some cases, smaller or larger window angles could be used to adjust the circumferential extent of the electrode surfaces to achieve a different degree of directionality. Window "angle" generally refers to the arc occupied by the window along the circumference of the insulating member.

The electrodes could be made longer in the axial direction (with a corresponding increase in window length) or larger in diameter, however, to compensate for the loss of surface area due to the reduced angle.

Figure 5:
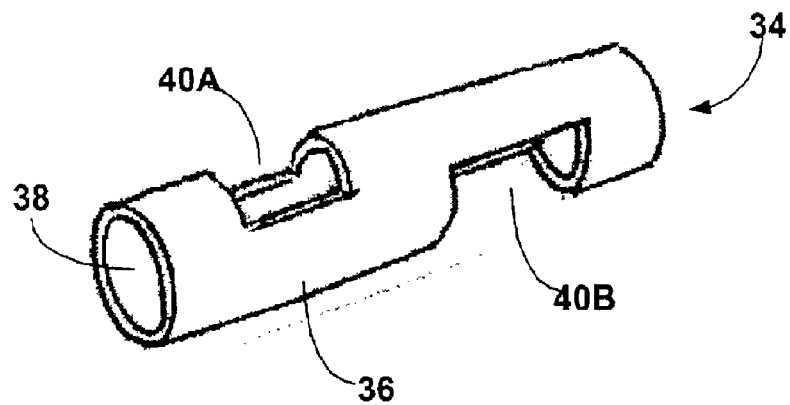
FIG. 5 is a perspective view of a windowed insulating member in accordance with one embodiment.

FIG. 5 is a perspective view of a windowed insulating member in accordance with a second embodiment. As shown in FIG. 5, insulating member 34 is substantially cylindrical and has a tubular body 36 that defines an inner lumen 36. Insulating member 34 conforms substantially to insulating member 10 of FIG. 1, but includes two windows 40A, 40B formed at different positions along the length of insulating member 34. In particular, in the example of FIG. 4, windows 40A, 40B are formed at different axial positions along the length of insulating member 34, and on opposite sides of the insulating member. In this manner, insulating member 34 provides multiple windows at different axial and circumferential positions to provide the surgeon with greater flexibility in lead positioning.

Figure 6:
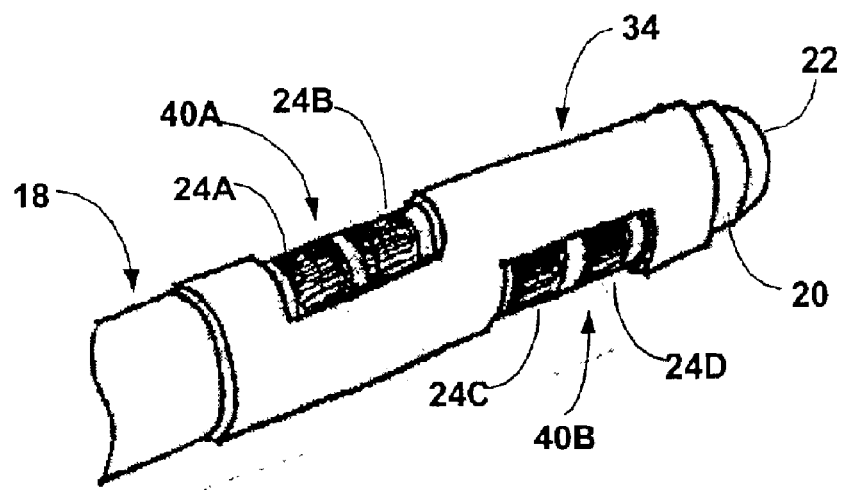
FIG. 6 is a perspective view illustrating a lead assembly incorporating the windowed insulating member of FIG. 5 and the deep brain stimulation lead of FIG. 2.

FIG. 6 is perspective view illustrating a lead assembly incorporating the windowed insulating member 34 of FIG. 5 and the deep brain stimulation lead 18 of FIG. 2. As shown in FIG. 6, windows 40A, 40B expose different electrodes 24. Window 40A exposes portions of electrodes 24A, 24B on a first side of lead 18. Window 40B exposes portions of electrodes 24C, 24D on a second, opposing side of lead 18. The arrangement shown in FIG. 6 permits independent directional stimulation of different or opposing brain structures or sections. With multiple windows 40A, 40B, the surgeon can achieve a different localized stimulation by programming a stimulation current generator to selectively energize electrodes 24.

Figure 7:
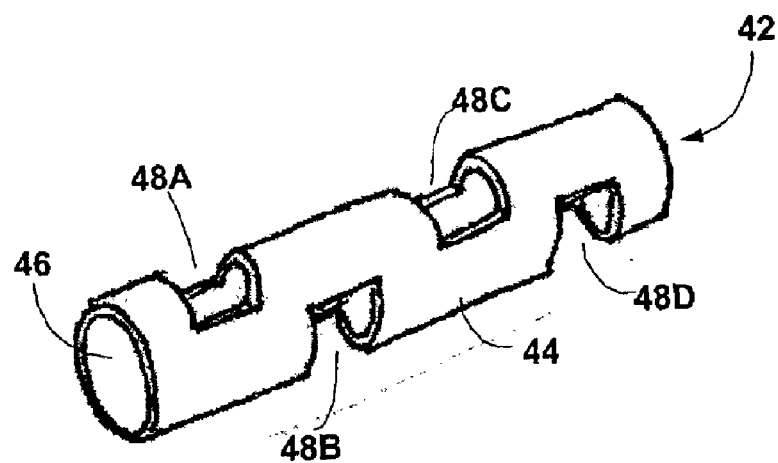
FIG. 7 is a perspective view of a windowed insulating member in accordance with an added embodiment.

FIG. 7 is a perspective view of a windowed insulating member 42 in accordance with a third embodiment. As shown in FIG. 7, insulating member 42 is substantially cylindrical and has a tubular body 44 that defines an inner lumen 46. Insulating member 42 conforms substantially to insulating member 34 of FIG. 5, but includes four windows 48A, 48B, 48C, 48D (hereinafter 48) formed at different positions along the length of insulating member 42.

Figure 8:
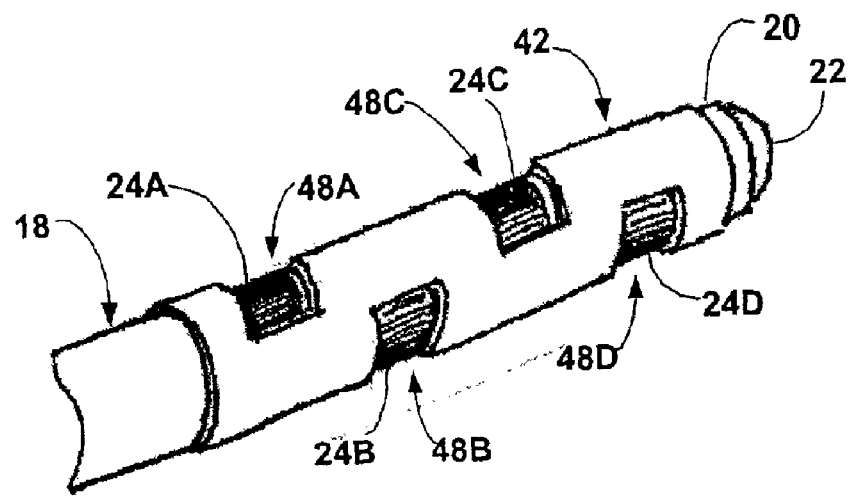
FIG. 8 is perspective view illustrating a lead assembly incorporating the windowed insulating member of FIG. 7 and the deep brain stimulation lead of FIG. 2.

FIG. 8 is a perspective view illustrating a lead assembly incorporating the windowed insulating member 42 of FIG. 7 and the deep brain stimulation lead 18 of FIG. 2.

Windows 48A, 48C may be formed on one side of insulating member 42 in alignment with electrodes 24A, 24C. Similarly, windows 48B, 48D may be formed on an opposite side of insulating member 42 in alignment with electrodes 24B, 24D. Each window 48 of insulating member 42 exposes a portion of an individual electrode 24, to provide a directional capability that can be applied on an electrode-by-electrode basis.

Figure 9:
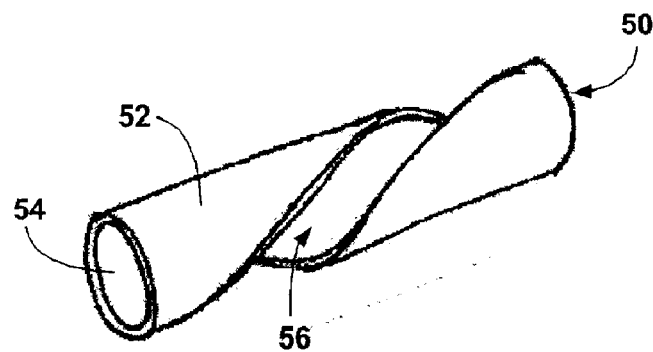
FIG. 9 is a perspective view of a windowed insulating member in accordance with another embodiment.

FIG. 9 is a perspective view of a windowed insulating member 50 in accordance with a fourth embodiment. As shown in FIG. 9, insulating member 50 has a tubular body 52 that defines an inner lumen 54. Insulating member 52 defines a single window 56 that is pitched, or "spiral," in its shape.

Figure 10:
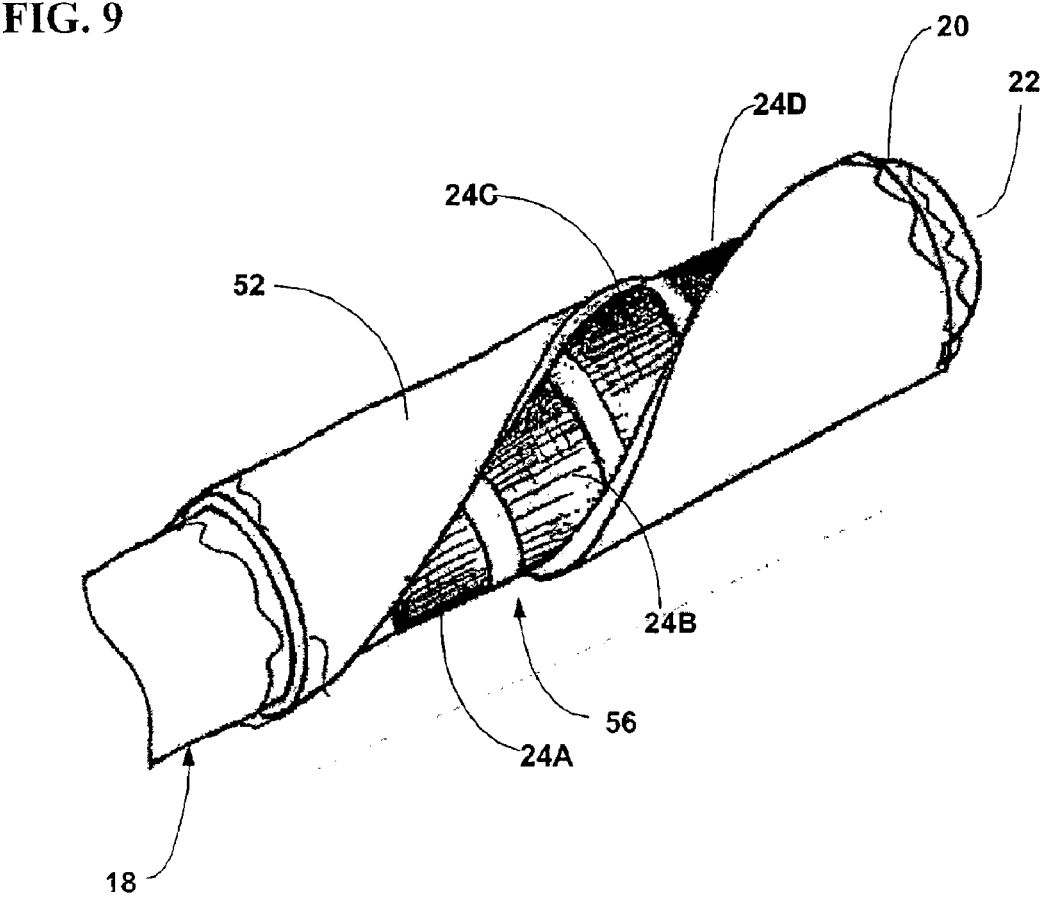
FIG. 10 is a perspective view illustrating a lead assembly incorporating the windowed insulating member of FIG. 9 and the deep brain stimulation lead of FIG. 2.

FIG. 10 is a perspective view illustrating a lead assembly incorporating the windowed insulating member of FIG. 9 and the deep brain stimulation lead of FIG. 2. Window 56 defines a spiral pattern that winds about insulating member 34 to expose different portions of electrodes 24 at different positions along the length of lead 10. The pitched configuration of window 56 can create a lead that not only allows directional current spread, but also compensation of the electrode depth in the axial lead direction simply by rotating the lead body during implantation.

Figure 11:
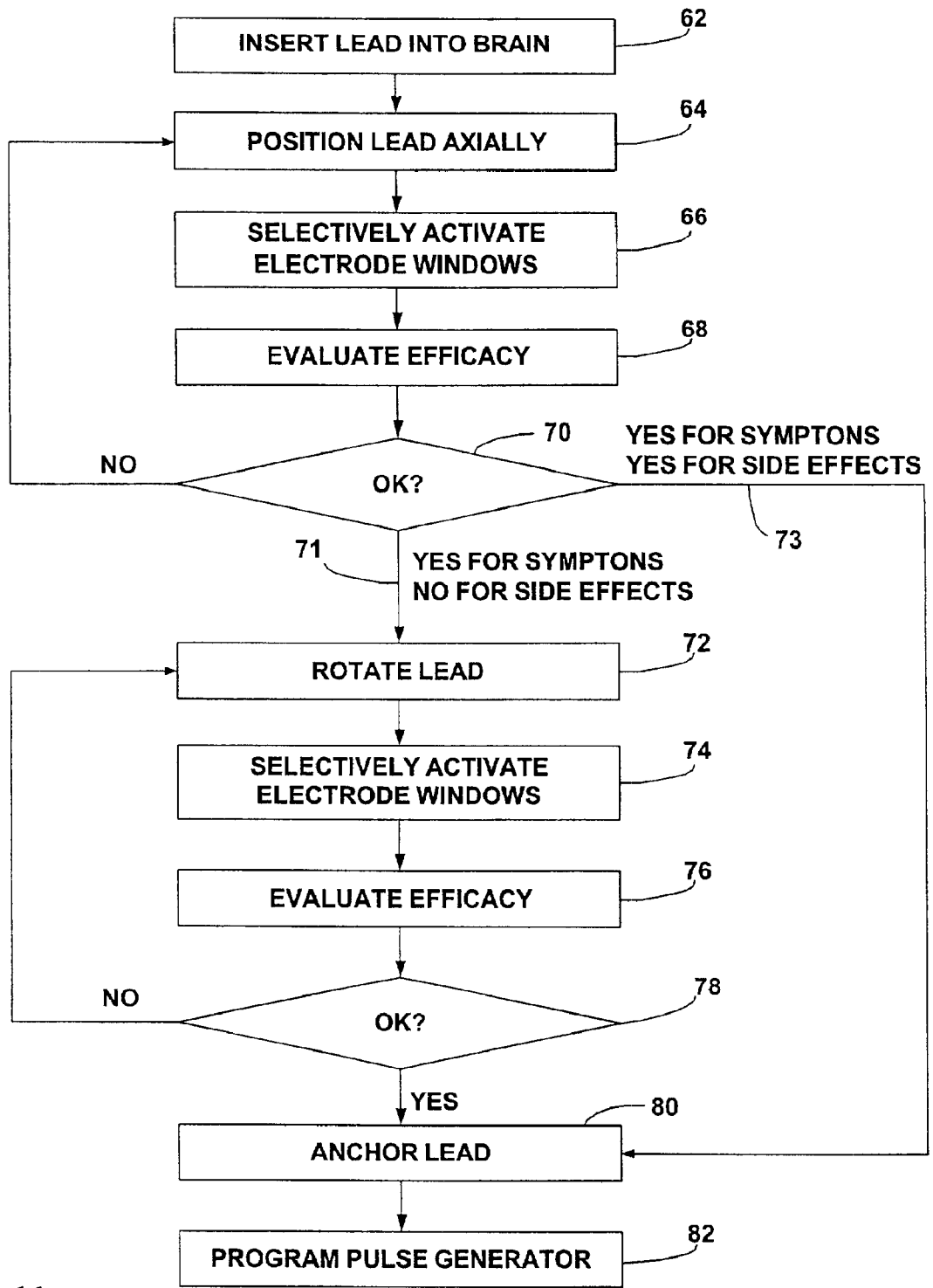
FIG. 11 is a flow diagram illustrating a method for deploying a deep brain stimulation lead constructed in accordance with the invention.

FIG. 11 is a flow diagram illustrating a method for deploying a deep brain stimulation lead constructed in accordance with the invention. Steps used to position the lead may conform substantially to those described in U.S. Pat. No. 5,843,148, entitled High Resolution Brain Stimulation Lead and Method of Use, to Gijsbers et al., the entire content of which is incorporated herein by reference. It is assumed that the patient has been prepared in a standard fashion, e.g., a burr hole has been drilled, a stereotactic frame is provided, and an anchoring system is ready. As shown in FIG. 11, the lead is inserted into the brain (62) and then positioned axially along the insertion path relative to a desired target (64). If the lead is equipped with multiple electrodes, the surgeon may selectively activate electrode windows individually or in combination to deliver electrical stimulation to a target with desired directionality (66).

Upon activating the electrode(s), the surgeon evaluates efficacy (68). In particular, the surgeon determines whether symptoms of the pertinent disorder have been satisfactorily alleviated, and whether undesirable side effects have been avoided. As an example, the therapy may be designed to alleviate rigidity, but also cause loss of control due to stimulation of tissues adjacent the desired target. If efficacy is not achieved (70), the surgeon may repeat the positioning and selective activation steps until the proper axial position and proper combination of electrode windows has been determined. If the surgeon observes that axial positioning of the lead has alleviated pertinent symptoms and avoided significant side effects (73), there may be no need to evaluate different rotational lead positions. In this case, the surgeon simply proceeds to anchor the lead (80).

If the symptoms are alleviated but undesirable side effects are produced following axial positioning (71), the surgeon may proceed to rotational positioning of the lead in an attempt to achieve efficacy. In particular, the surgeon may rotate the lead (72), selectively activate the electrode windows (74) and evaluate efficacy (76). The surgeon may evaluate different rotational positions in an effort to reduce potential side effects induced by the stimulation of brain structures adjacent to the desired target. Like axial positioning, this rotational adjustment and associated selection of electrodes may be an iterative process. Once the desired effects are achieved (78), the surgeon anchors the lead (80) and programs the pulse generator to drive the selected combination of electrodes (82). If the desired effects are not achieved, the surgeon may continue evaluation of different rotational lead positions as shown in FIG. 11, or choose to reinitiate evaluation of alternative axial lead positions.

As a variation of the method of FIG. 11, a lead may first be inserted without a windowed insulating member. In some instances, the surgeon may achieve satisfactory results in alleviating symptoms and avoiding undesirable side effects without the need for an insulating member that provided directionality. In particular, the surgeon may evaluate the efficacy of the lead in different axial and rotational positions. If satisfactory results are not achieved, the lead may be withdrawn from the implantation site and fitted with a windowed insulating member as described herein. In this manner, the surgeon transforms the lead into a directional lead. Then, the surgeon may reinsert the lead using the same implantation channel as used for the lead previously inserted without the insulating member, and manipulate the lead to evaluate the results. Thus, the insulating member may be an optional component that is used either on a first implantation attempt or a subsequent implantation attempt.

The use of windows to expose portions of the electrodes, in combination with axial and rotational adjustment and electrode selection, provide the surgeon with a variety of options in delivering the desired treatment to a small, localized target in the brain. In particular, the treatment can be made highly directional, and is susceptible to fine tuning using a combination of the above parameters. In addition to increasing flexibility of treatment, the present invention can serve to relax some of the positional tolerances ordinarily imposed on the surgeon in placement of the lead within the brain. If the stimulation energy is not delivered ideally, the surgeon may experiment with not only different rotational positions and axial positions but also different windowed insulating members with a variety of patterns.

Figure 12:
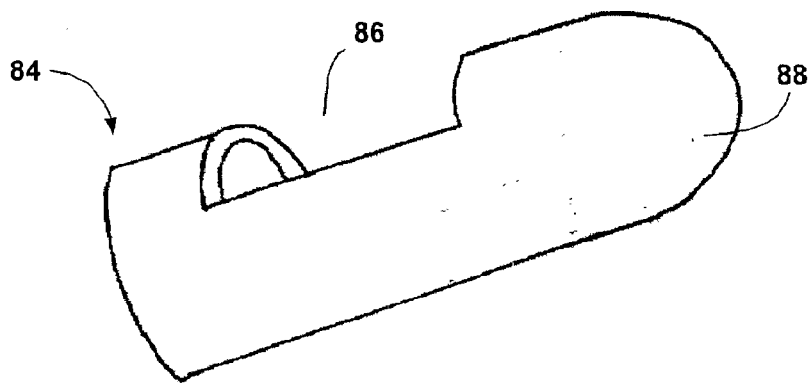
FIG. 12 is a perspective view of a windowed insulating member in accordance with a further embodiment.
Figure 13:
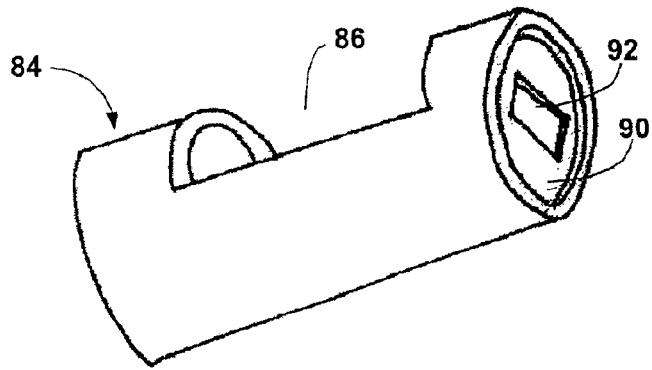
FIG. 13 is a perspective view illustrating an interior portion of the insulating member of FIG. 12.

FIG. 12 is a perspective view of a windowed insulating member 84 in accordance with a further embodiment. Insulating member 84 defines a window 86 and may include a rounded tip 88. FIG. 13 is a partial perspective view illustrating an interior portion of insulating member 84. As shown in FIG. 13, insulating member 84 includes an interior cross-sectional wall 90 that extends within the insulating member in a direction transverse to the axial length of the insulating member. Wall 90 defines an interlock aperture 92 designed to receive a locking member from a lead. Together, aperture 92 and the locking member form an interlocking structure that substantially fixes insulating member 84 in place relative to a lead body.

Figure 14:
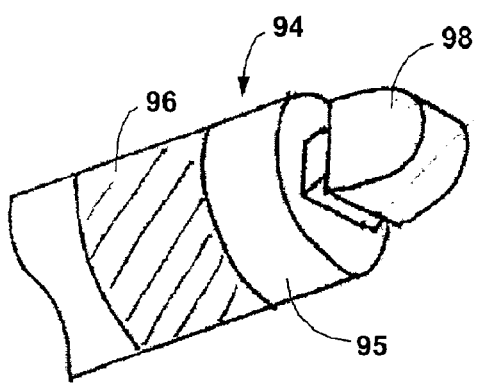
FIG. 14 is a perspective view of an example stimulation lead suitable for use with the insulating member of FIG. 12.

FIG. 14 is a perspective view of an example stimulation lead 94 suitable for use with insulating member 84 of FIG. 12. Lead 94 includes a lead body 95 carrying an electrode 96. Lead body 95 may carry a number of electrodes, although single electrode 96 is shown for purposes of example. In addition, a distal tip of lead body 95 carries a locking member 98 that protrudes outward along the longitudinal axis of lead 94. Locking member 98 may be formed, for example, by molding.

Figure 15:
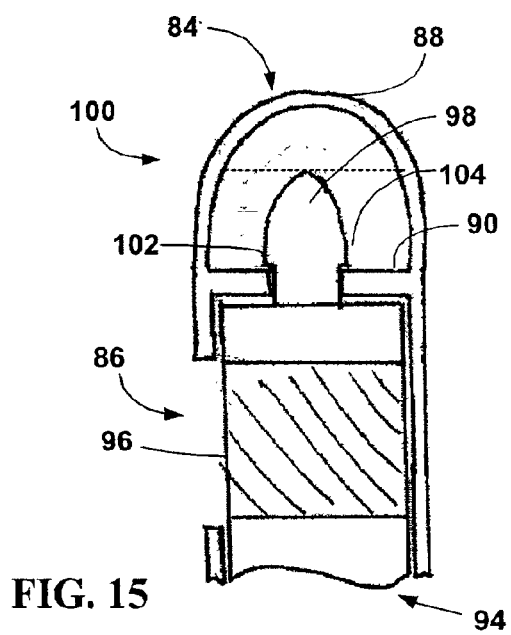
FIG. 15 is a cross-sectional side view of a lead assembly incorporating the insulating member of FIG. 12 and the lead of FIG. 14.

FIG. 15 is a cross-sectional side view of a lead assembly 100 incorporating the insulating member 84 of FIG. 12 and lead 94 of FIG. 14. As shown in FIG. 15, insulating member 84 is placed over lead 94. Insulating member 84 and lead 94 are urged toward each other in opposite directions to push locking member 98 through interlock aperture 92. Wall 90 may be made somewhat flexible to permit it to be biased upward as locking member 98 is pushed into interlock aperture 92, and thereby provide clearance for the locking member.

Once locking member 98 is pushed through interlock aperture 92, e.g., providing a snap-fit flange surfaces 102, 104 bear against one surface of wall 90 to limit axial movement of lead 94 away from distal tip 88 of insulating member 84. An upper surface 106 of lead body 95 bears against an opposing surface of wall 90 to limit axial movement of lead 94 toward distal tip 88. In addition, interlock aperture 92 and locking member 98 can be "keyed," e.g., using the rectangular configuration shown in FIG. 13, to prevent rotational movement between lead 84 and insulating member 84. Insulating member 84 can be attached very quickly to the distal end of lead 94, and thereby bring window 86 into ready alignment with electrode 96.

Insulating member 84 and lead 94, as shown in FIGS. 12–15, provide a quick-attach configuration that permits quick and simple conversion to make the lead directional. The surgeon may elect to implant a directional lead initially or following insertion of a non-directional lead with unsatisfactory results. The simple and convenient interlocking arrangement of insulating member 84 and lead 94 permits the surgeon to act quickly in deploying the directional lead without the need for adhesives and the like.

FIG. 16 is a perspective view of a stimulation lead 94 with a locking member and an end-cap 97. End-cap 97 covers the locking member when stimulation lead 94 is used in a non-directional mode. For example, end-cap 97 may be press-fit, snap-fit or adhesively bonded over the distal tip of electrode 94. Notably, end-cap 97 may have a generally atraumatic, rounded tip. FIG. 17 is another perspective view of the lead assembly of FIG. 15, for use in a directional mode.

Figure 18:
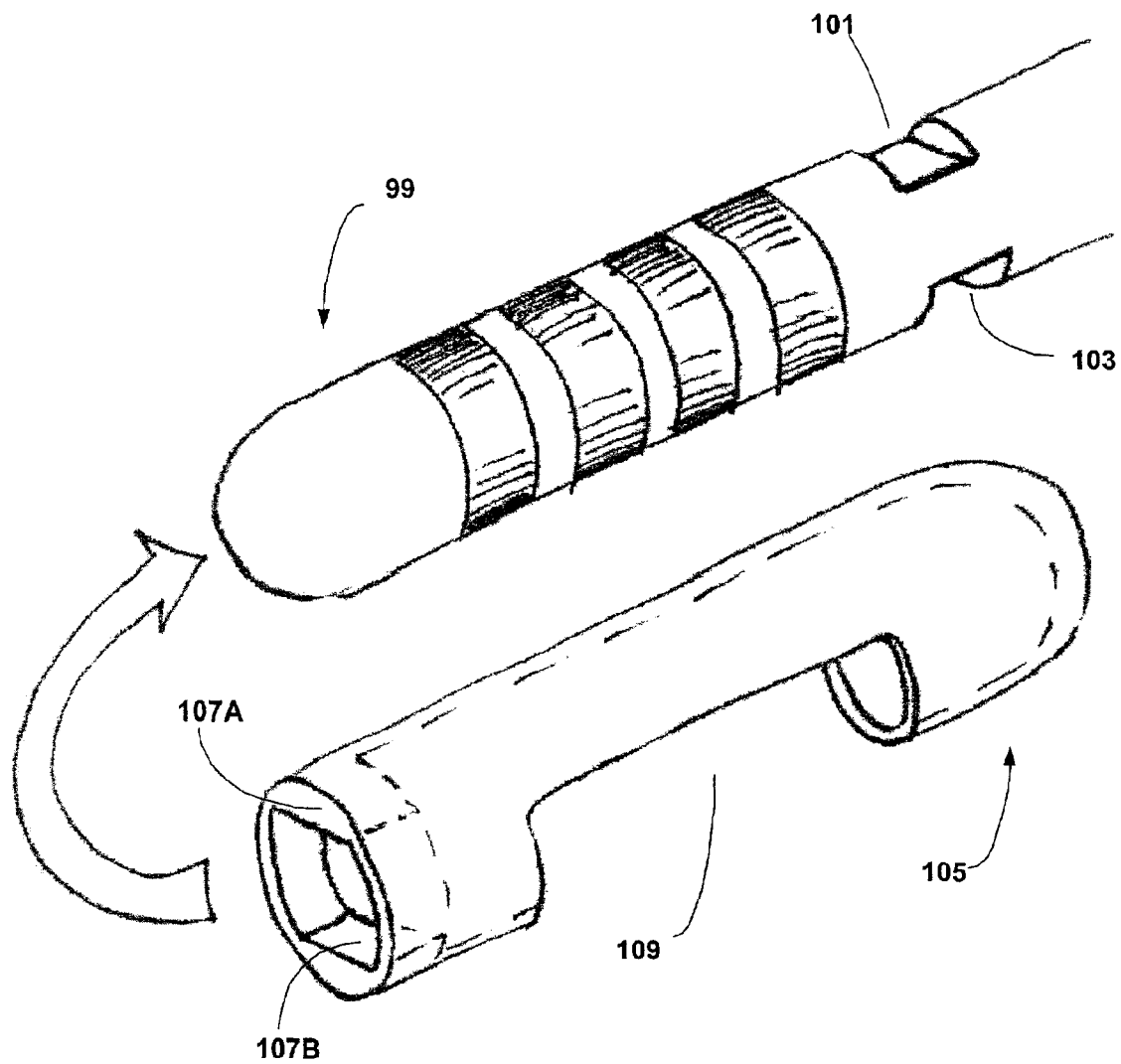
FIG. 18 is a perspective view of another embodiment of a stimulation lead.

FIG. 18 is a perspective view of another embodiment of a stimulation lead 99. As shown in FIG. 18, stimulation lead may include one or more detents 101, 103 that engage surfaces 107A, 107B formed in insulating member 105. Insulating member 105 includes a window 109. When insulating member 105 is placed over lead 99, surfaces 107A, 107B on the interior of the insulating member lock into place in detents 101, 103, e.g., via a snap fit, to fix the insulating member relative to the lead and, more particularly, place window 109 in alignment with a number of electrodes carried by the lead.

Figures 19, 20:
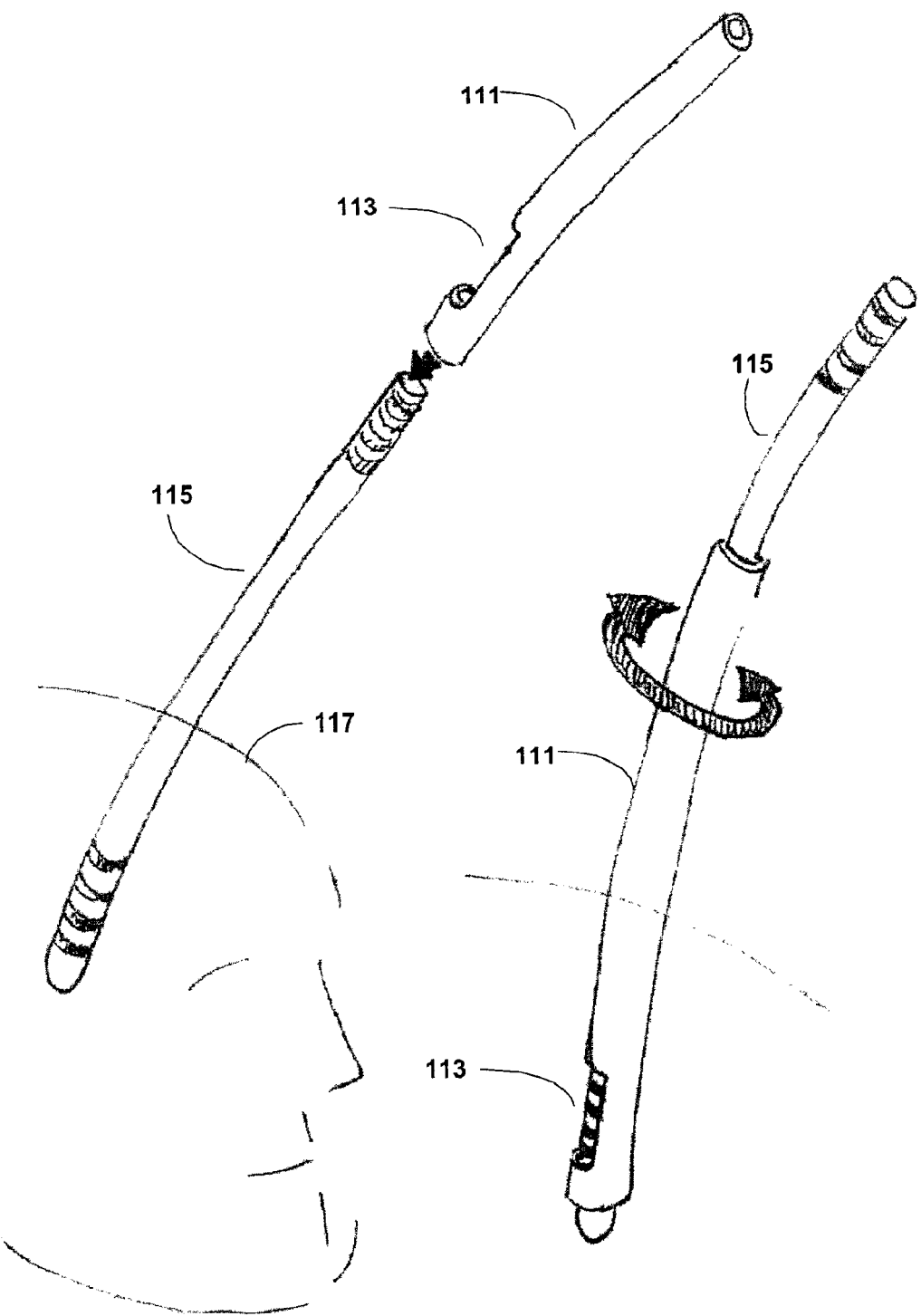
FIG. 19 is a perspective view of a stimulation lead in combination with a longer insulating member.
FIG. 20 is a perspective view of the lead and insulating member of FIG. 19 in operation.

FIG. 19 is a perspective view of a stimulation lead 115 in combination with a longer insulating member 111 having a window 113. In this example, insulating member 111 may have an increased length that covers a major portion of the length of lead 115. FIG. 20 is a perspective view of the lead and insulating member of FIG. 19 in operation. As illustrated in FIG. 20, insulating member 111 may slide into place over lead 115 so that window 113 aligns with one or more electrodes near the distal tip of the lead. However, a portion of insulating member 111 may extend outward from the implanted environment, permitting a surgeon to rotate the insulating member without necessarily rotating lead 115, to thereby adjust the directionality of the lead. Insulating member 111 may then be crimped or bonded in place, for example, to fix the insulating member both rotationally and axially relative to lead 115.

Figure 21:
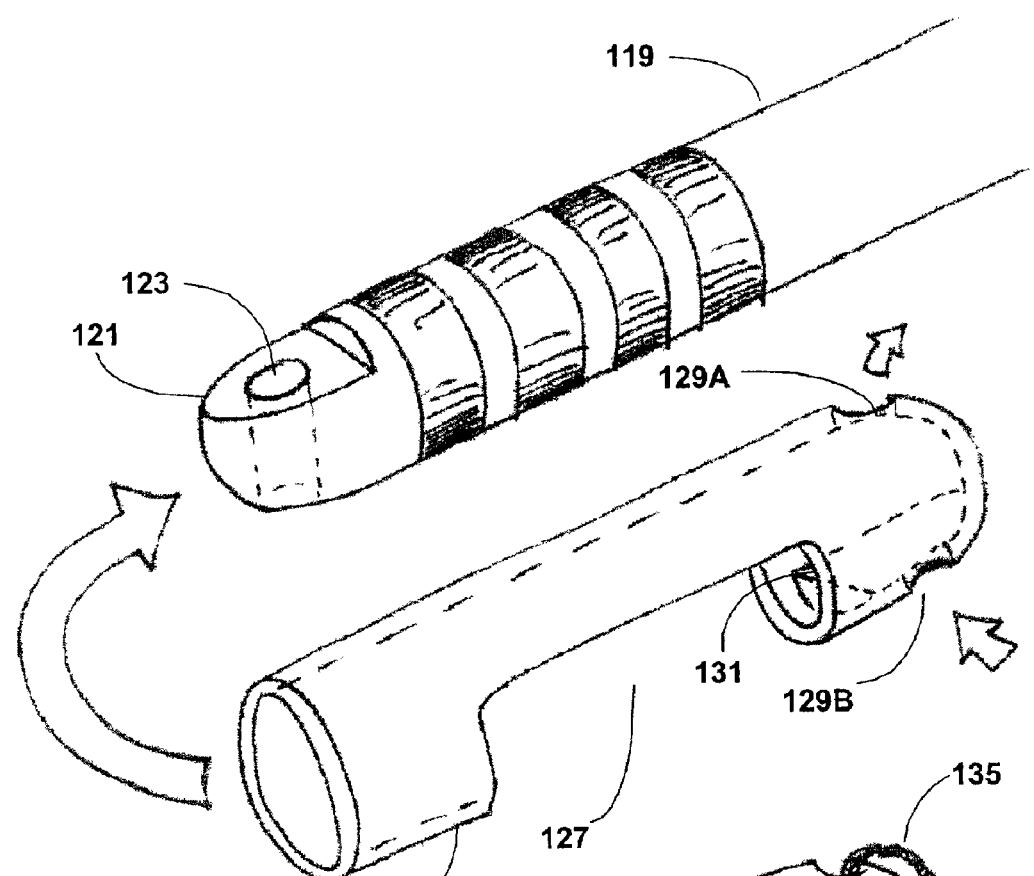
FIG. 21 is a perspective view of another lead assembly with an alternative insulating member.
Figure 22:
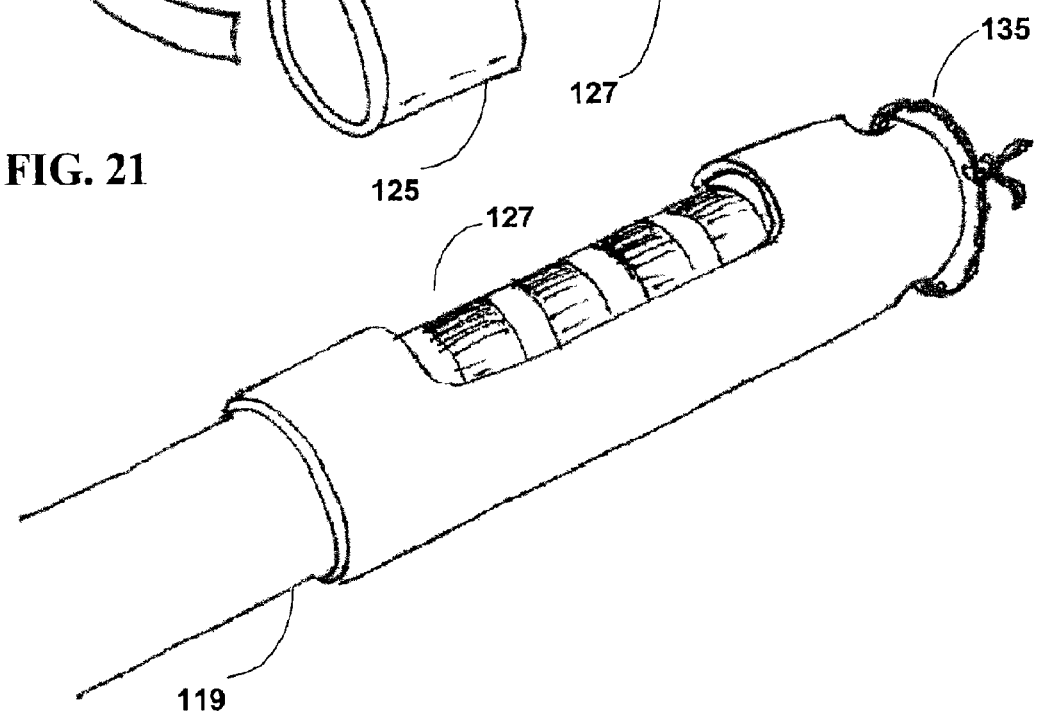
FIG. 22 is a perspective view of the lead assembly of FIG. 21 in operation.

FIG. 21 is a perspective view of another lead assembly with an alternative insulating member. In the example of FIG. 21, a lead 119 includes a distal lead tip with a recessed area 121 and a hole 123 that extends through the lead tip in a direction transverse to the longitudinal axis of lead 119. An insulating member 125 defines a window 127 and a hole with openings 129A, 129B on opposite sides of a the distal tip of the insulating member. A raised surface 131 is provided inside the distal tip of insulating member 125 for engagement with recessed area 121. FIG. 22 is a perspective view of the lead assembly of FIG. 21 in operation. As shown in FIG. 22, openings 129A, 129B in insulating member 125 and hole 123 in lead 119 may permit a suture 135 to be passed through the insulating member and the lead to anchor the lead in place.

FIG. 23 is a perspective view of a lead assembly with a shouldered tip. The lead assembly of FIG. 23 corresponds substantially to the lead assembly of FIGS. 19 and 20. However, lead 137 includes a shouldered tip 141 with a ridge 143 for abutment with insulating member 139 to thereby limit distal travel of the insulating member. FIG. 24 is a perspective view of the lead 137 of FIG. 23 in combination with the insulating member 139. As shown in FIG. 23, insulating member 139 may have an increased length to cover a substantial portion of lead 137 and extend outward from the implanted environment. Insulating member 139 defines a window 145 to expose portions of one or more electrodes carried by lead 137. FIGS. 25 and 26 illustrate the lead assembly of FIG. 23 in operation. As shown in FIG. 26, in particular, insulating member 139 may include an additional window 147 that receives a suture 149 or other fixation device to further prevent rotation of the insulating member about lead 137.

Figure 27:
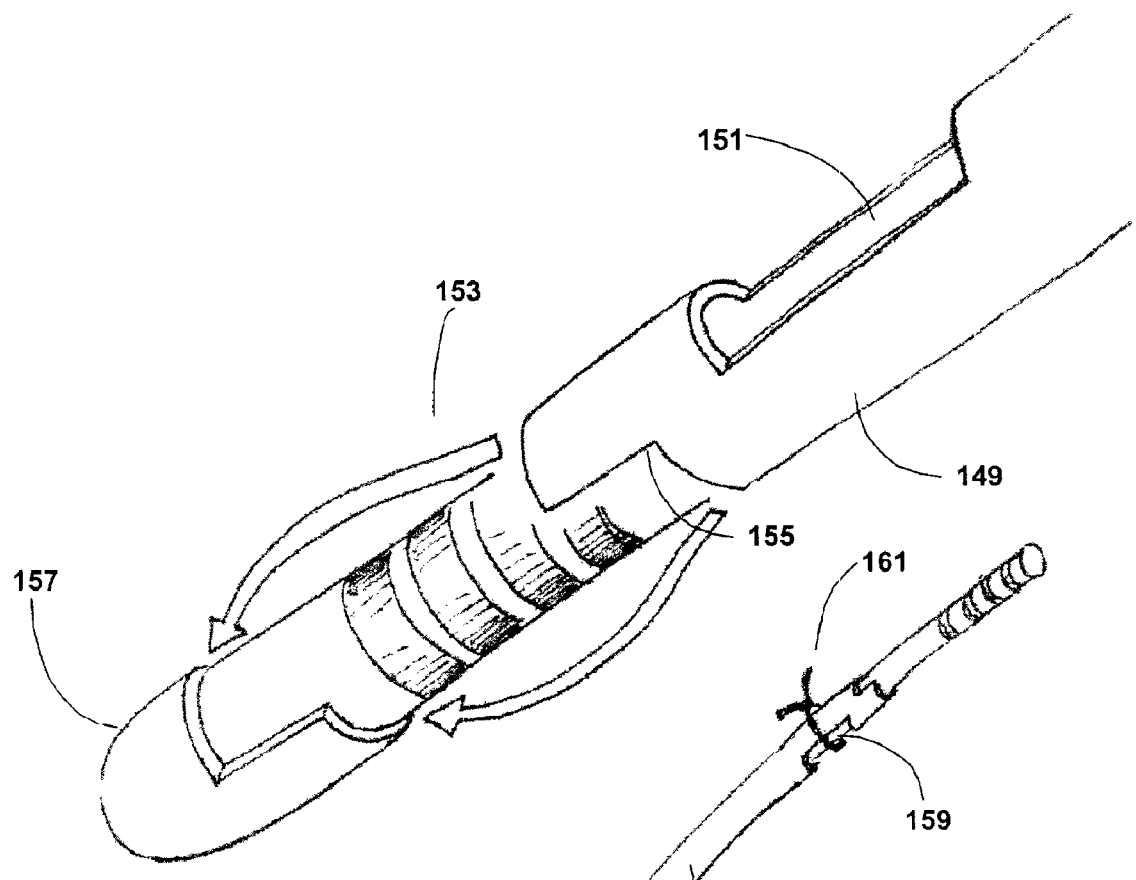
FIG. 27 is a perspective view of another embodiment of a lead assembly with an alternative interface with an insulating member.
Figure 28:
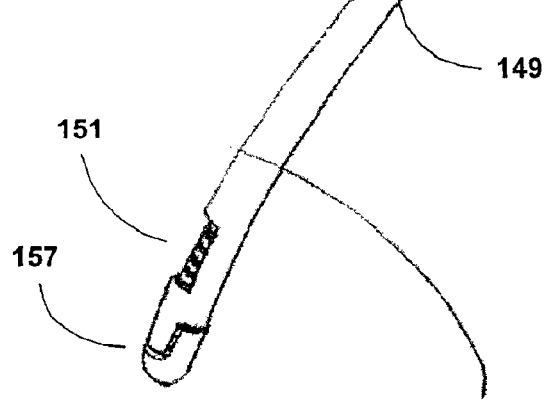
FIG. 28 illustrates the lead assembly of FIG. 27 in operation.

FIG. 27 is a perspective view of another embodiment of a lead assembly with an alternative interface with an insulating member. Insulating member 149 defines a window 151 and a stepped interface 155. The tip of lead 153 defines a reciprocal stepped interface 157 that engages stepped interface 155 of insulating member 149 to limit axial and rotational travel of the insulating member. FIG. 28 illustrates the lead assembly of FIG. 27 in operation. As shown in FIG. 28, insulating member 149 may include an additional window 159 that receives a suture 161 or other fixation device to prevent rotation of the insulating member about lead 153.

FIG. 29 is a side view of an electrical stimulation lead 106 having a lead body 108 with at least one distal electrode and at least one intermediate electrode in accordance with another embodiment. In the example of FIG. 29, lead 106 includes four distal electrodes 110A, 110B, 110C, 110D for electrical stimulation of a target within the brain. Any of electrodes 110 may function as a recording electrode instead of or in addition to a stimulation electrode. Lead 106 also includes an intermediate electrode 112. Lead 106 may be configured for a particular stimulation application involving stimulation of an intermediate target at a first depth within the brain using intermediate electrode 112 and stimulation of a deep brain target at a second depth within the brain using distal electrodes 110.

FIG. 30 is a side view of lead 106 of FIG. 29 incorporating a windowed insulating member 114 that is slidable to expose a portion of the intermediate electrode of FIG. 29. In FIG. 30, reference numeral 115 represents the cranium of a patient. As shown in FIG. 30, lead 106 is inserted to a desired depth within the brain so that intermediate electrode 112 is axially aligned with a first target 116 and distal electrodes 110 are axially aligned with a second target 118.

For one stimulation procedure, first target 116 may be the motor cortex whereas second target 118 may be the Globus Pallidum Internae (Gpi). Areas of the motor cortex, which are involved in the control of movement in the muscle of the thumb can be activated if the appropriate stimulation is applied in the correct area of the GPi. If postural instability of the patient is a major Parkinsons Disease symptom, optimizing the excitability of those parts of the motor cortex which control movement of leg muscles with intermediate electrode 112 may be helpful in finding the optimal physiological target for the distal electrodes 110.

With lead 106, during a procedure for finding the optimal physiological target for distal electrodes 110, the surgeon may use intermediate electrode 112 as a test stimulation electrode. In the neighborhood of the expected optimal physiological target, along the insertion trajectory of intermediate electrode 112, the surgeon stimulates the motor cortex while he evaluates the effect of this stimulation upon, for example, muscle rigidity in the affected limb.

The stereotactic trajectory of lead 106 is such that distal electrodes 110 pass through the expected anatomical target. This leaves one degree of freedom for this trajectory, namely the insertion point of lead 106 at the skull. This means that the intermediate electrode may also be inserted in such a way that it goes through the relevant part of the motor cortex, i.e., first target 116, on its way to the anatomical target of lead 106, i.e., second target 118. A technique and lead assembly designed for intersection of the motor cortex and the Gpi is described in U.S. Pat. No. 6,253,109, to Gielen, the entire content of which is incorporated herein by reference. Once implanted, it is possible to stimulate both the first and second targets 116, 118, e.g., at the deep brain target and at the motor cortex.

The distance between the optimal deep brain target and the relevant motor cortex target is not the same in each patient. To accommodate different distances, insulating member 114 can be made slidable to expose different portions of intermediate electrode 112. As shown in FIG. 30, insulating member 114 includes a window 120 that selectively exposes intermediate electrode 112 at different distances relative to cranium 115. In this manner, lead 106 enables the evaluation of the motor cortex excitability in an intra-operative as well as post-operative situation. This excitability of the motor cortex is an objective criteria for the correct placement of distal electrodes 110 of lead 106, e.g., in the GPi or an objective criteria for optimal stimulation parameter settings. A second windowed insulating member 122 may define windows for exposure of portions of distal electrodes 110, as further shown in FIG. 30.

Figure 31:
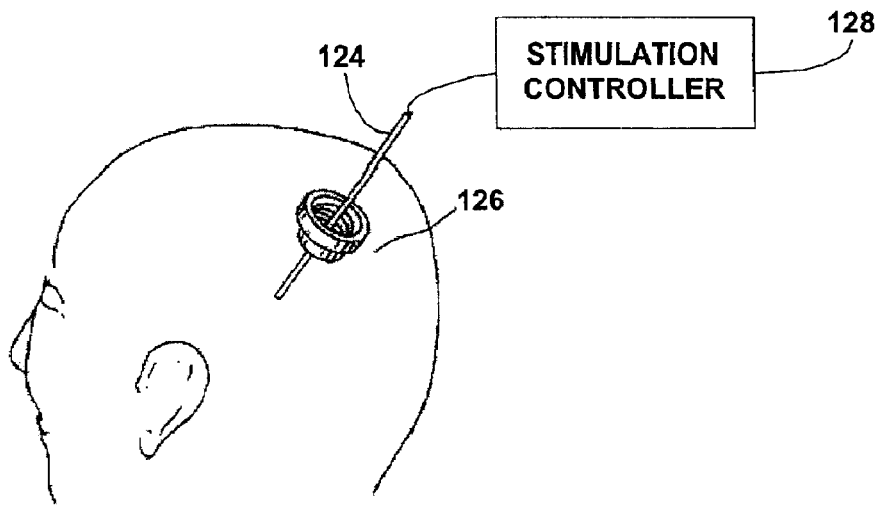
FIG. 31 illustrates insertion of a lead as described herein into a patient's brain via a burr hole placed in the cranium.

FIG. 31 illustrates insertion of a lead as described herein into a patient's brain via a burr hole placed in the cranium. As shown in FIG. 31, a lead 124 is inserted through burr hole 126. Lead 124 is electrically coupled to a stimulation controller 128 that supplies stimulation current to various electrodes carried by lead 124. In addition, stimulation controller 128 may receive signals from one or more of the electrodes to sense and record brain activity proximate to a desired target. Stimulation controller 128 may be either external to the patient or implantable.

Figure 32:
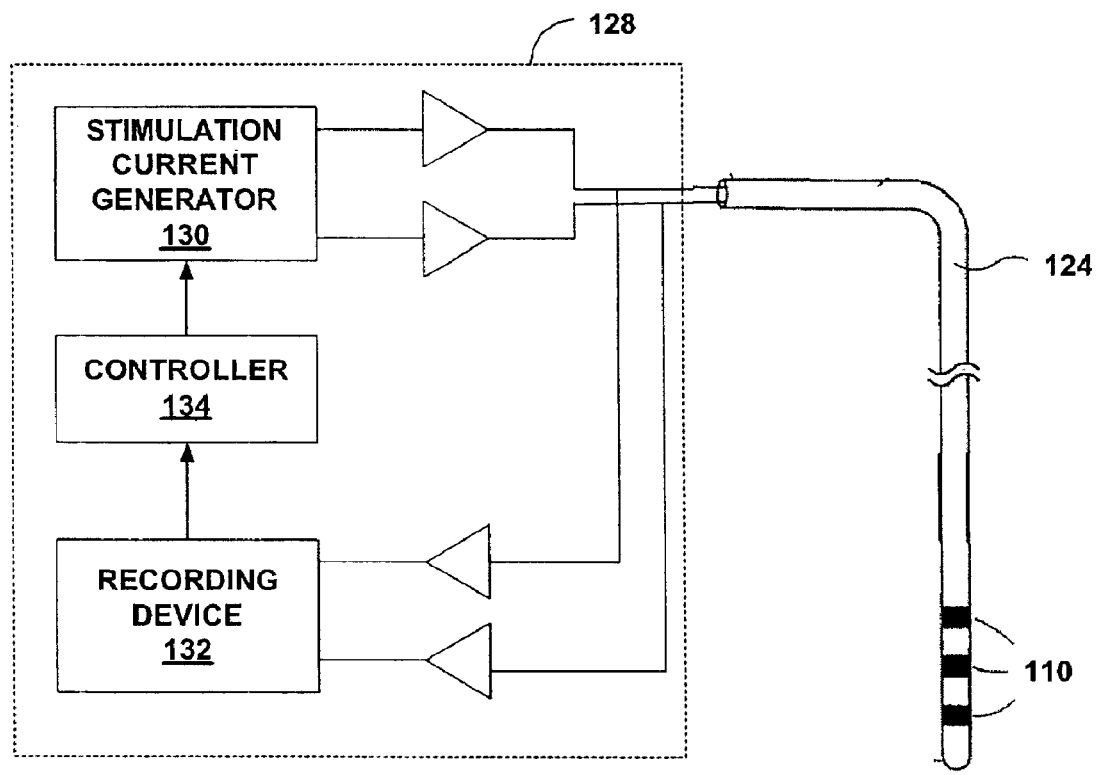
FIG. 32 is a functional block diagram illustrating a stimulation controller.
Figure 33A:
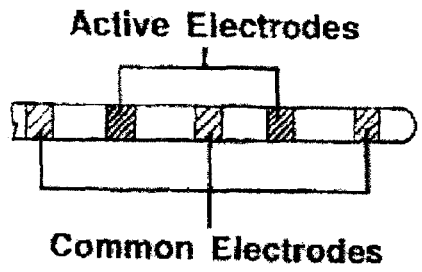
FIGS. 33A–33F show some different embodiments of a lead and electrode sets of the present invention for applying steered pulses to one or more brain targets.
Figure 33B:
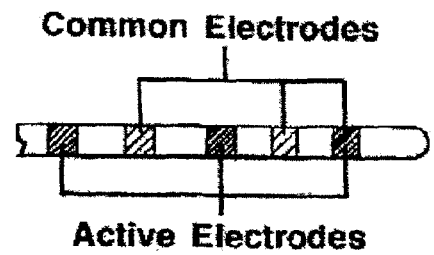
Figure 33C:
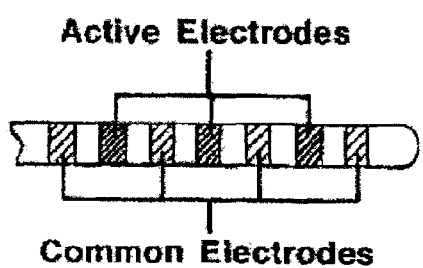
Figure 33D:
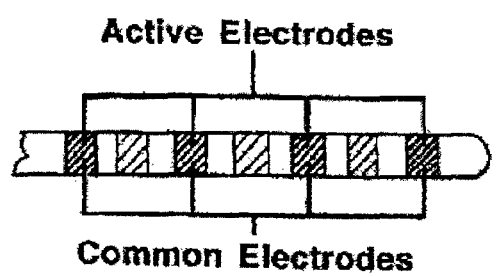
Figure 33E:
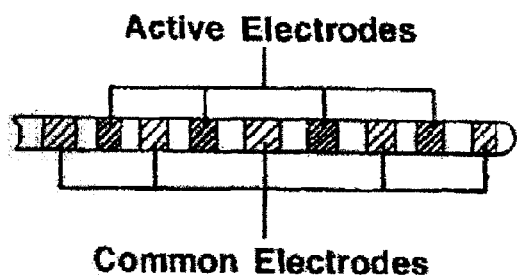
Figure 33F:
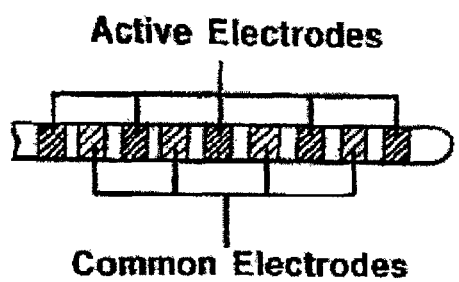

FIG. 32 is a functional block diagram illustrating stimulation controller 128 in greater detail. As shown in FIG. 32, stimulation controller 128 may include a stimulation current generator 130, a recording device 132, and a controller 134. In operation, recording device 132 records signals obtained from one or more electrodes carried by lead 124. The recorded signals may be used for analysis, triggering of stimulation current generator 130 or both. For example, controller 134 may be responsive to brain activity signals sensed by recording device 132 via lead 124, and thereby activate stimulation current generator 130 to deliver electrical stimuli to one or more electrodes carried by lead 124.

In the example of FIG. 32, two conductors are shown. However, the number of conductors, and associated sensing and current output channels, may vary. Stimulation controller 128 may be, for example, a Medtronic Model 3628, or a modification of that device. Controller 134 may utilize a microprocessor and/or other control and timing circuitry. In addition, controller 134 may control switching circuitry to switch the output of stimulation current generator 130 between different conductors that carry stimulation current to the lead electrodes.

In any selected lead and electrode configuration of the present invention, appropriate control of individual pulse component parameters applied to each of the electrodes can be utilized substantially as described in U.S. Pat. No. 5,800,645 to cause a resulting composite pulse to be steered to a desired location. In other words, steering techniques can be used to adjust the stimulation pulse parameters, e.g., pulse width, amplitude, frequency, and the like, applied to the individual electrodes to achieve an effective composite pulse. In this way, if the lead shifts position over time, and as a result stimulation efficiency decreases, individual pulse parameters may be re-programmed so that a composite stimulation pulse is once again delivered with optimum efficiency and let positional accuracy. Thus, steering and directionality can be provided in combination. In some embodiments, the stimulation controller may re-program itself by modifying individual pulse parameters on a periodic or on-going, continual basis so that optimum delivery of stimulation pulses is maintained, even though the lead shifts position.

In any particular electrode configuration, selected or additional electrodes may sense brain activity signals. The electrode sets may comprise a varied number of electrodes may be switchable in conjunction with a common reference potential provided, for example, by an external electrode or a stimulation controller case as a common electrode.

As shown in FIGS. 33A–33F, for example, electrode sets provided with the leads described herein may comprise three active electrodes separated by two common electrodes, three active electrodes positioned between four common electrodes where all active electrodes are disposed between two outlying common electrodes, four active electrodes separated by three common electrodes, four active electrodes positioned between five common electrodes where all active electrodes are disposed between two outlying common electrodes, and so forth.

Electrodes carried by a lead as described herein may be used to deliver a variety of stimulation currents to a desired target in the brain, and thereby deliver a variety of therapies, e.g., as described in U.S. Pat. No. 5,843,148, U.S. Pat. No. 6,011,996, U.S. Pat. No. 6,253,109, and U.S. Pat. No. 6,319,241, the content of each of which is incorporated herein in its entirety. The stimulation current may take the form of a pulse pattern emitted by one or more electrodes in a synchronized or unsynchronized manner. For example, the pulse pattern of electrical stimuli can include pairs of two or more electrical stimuli delivered from different electrode pairs to the brain structure. Alternatively, the pulse pattern of electrical stimuli can be a short train, or burst, of a predetermined number of stimuli. The exact pattern and number of electrical stimuli in the pulse pattern may be selected based in part on the brain structure to which the stimuli are delivered, and the particular brain disorder to be treated. In one embodiment, the pulse pattern may be repeated such that the electrical stimuli are continuously delivered to the patient.

The pulse pattern may be a pair of stimuli delivered to the brain structure. In this example, the pair of stimuli includes a first and a second stimulus, where the stimuli are delivered by different electrode pairs and separated by a predetermined time interval. The predetermined time interval may be a value in the range of approximately 5 to 2000 milliseconds. The specific time interval used depends upon the brain structure being treated, and may be a programmable value.

Additional electrical stimulus parameters are also programmable. Exact parameter values are specific for the brain structure involved. For example, the duration of each stimulus can be selected to fall in a range of approximately 30 microseconds to 10 milliseconds. Additionally, the waveform shape of the stimuli can also be programmed. Waveform shapes can include, but are not limited to, rectangular, sinusoidal and/or ramped shapes Other known waveform shapes can also be useful.

The magnitude of each stimulus of the pulse pattern may also be a selectable value in a range of approximately 10 microamperes to 10 milliamperes. Also, the pulse pattern of electrical stimuli may be delivered two or more times. In one embodiment, the pulse pattern may be repeatedly delivered to the patient in order to continuously treat the patient. The repeated delivery of the pulse pattern may include a repetition frequency, where the repetition frequency is programmed in the range of approximately 1 second to 30 minutes. Other values are also possible.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to lead configurations with cylindrical ring electrodes. In some embodiments, machined C-shaped ring electrodes could be embedded in a lead body to form selected electrode surfaces without windowing techniques. In this case, the electrode surface could be made flush or even protruded relative to the surface of the lead body, if desired. The present invention includes within its scope methods of implanting, using and making the leads described hereinabove.

All printed publications referenced hereinabove, including all patents and patent applications, are hereby incorporated by reference into the specification hereof, each in its respective entirety.

As those skilled in the art will appreciate readily upon reading the Summary of the Invention, the Detailed Description of the Preferred Embodiments and the Claims set forth below, at least some of the devices and methods disclosed in the patents referenced herein may be modified advantageously in accordance with the teachings of the present invention.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable brain stimulation lead comprising:
   a substantially cylindrical lead body having a proximal end, a distal end, and a plurality of substantially ring-like electrodes each having an arc or circumference extending substantially around the lead body; and
   an electrically insulating member that extending over at least body to cover at least covered portions of the circumference of the electrodes, and defining a plurality of windows that expose exposed portions of the circumference of the electrode, thereby increasing directionality of stimulation current delivered by the electrode, wherein the insulating member is formed as a sleeve-like member that extends over a portion of the lead body;
   wherein at least two windows are defined at different axial and circumferential positions about the lead body.

2. The lead of claim 1, wherein the insulating member is coated onto the lead body to define the window.

3. The lead of claim 1, wherein the sleeve-like member has a generally tubular configuration defining a lumen for receiving the lead body.

4. The lead of claim 3, wherein the sleeve-like member is molded to define the at least two windows.

5. The lead of claim 3, wherein the sleeve-like member is cut to define the at least two windows.

6. The lead of claim 1, wherein each electrode extends approximately 360 degrees about the lead body.

7. The lead of claim 1, wherein the lead body includes four electrodes, and the insulating member defines four windows.

8. The lead of claim 1, wherein the at least two windows each has a shape selected from the group consisting of a rectangle, square, oval and circle.

9. The lead of claim 8, wherein the at least two windows each has a shape selected from the group consisting of a rectangle and a square.

10. The lead of claim 8, wherein the at least two windows each has a shape selected from the group consisting of an oval and a circle.

11. The lead of claim 10, wherein the insulating sleeve-like member has a generally tubular configuration defining a lumen for receiving the lead body.

12. The lead of claim 11, wherein the sleeve-like member is molded to define the at least two windows.

13. The lead of claim 11, wherein the sleeve-like member is cut to define the at least two windows.

14. The lead of claim 1, wherein the lead body has a diameter of approximately 1.1 to 1.5 mm and the electrode has a length, extending longitudinally relative to the lead body, of approximately 1.3 to 1.7 mm.

* * * * *

UNITED STATES PATENT AND TRADEMARK OFFICE
CERTIFICATE OF CORRECTION

| | | |
|---|---|---|
| PATENT NO. | : 7,212,867 B2 | Page 1 of 1 |
| APPLICATION NO. | : 10/008773 | |
| DATED | : May 1, 2007 | |
| INVENTOR(S) | : van Venrooij et al. | |

It is certified that error appears in the above-identified patent and that said Letters Patent is hereby corrected as shown below:

Col. 16, Line 14: "at least body" should read --at least a portion of the lead body--

Signed and Sealed this

Sixth Day of November, 2007

JON W. DUDAS
*Director of the United States Patent and Trademark Office*